United States Patent [19]
Osypka

[11] Patent Number: 5,261,417
[45] Date of Patent: Nov. 16, 1993

[54] CARDIAC PACEMAKER LEAD WITH PROTECTED FIXED TISSUE SECURING MEANS

[76] Inventor: Peter Osypka, Basler Strasse 109, D-7889 Grenzach-Wyhlen, Fed. Rep. of Germany

[21] Appl. No.: 804,824

[22] Filed: Dec. 6, 1991

[30] Foreign Application Priority Data

Dec. 14, 1990 [EP] European Pat. Off. .......... 90 124185

[51] Int. Cl.$^5$ .............................................. A61N 1/05
[52] U.S. Cl. ..................................................... 607/127
[58] Field of Search ...................... 128/785, 419 P, 642

[56] References Cited

U.S. PATENT DOCUMENTS

| | | | |
|---|---|---|---|
| 4,311,153 | 1/1982 | Smits | 128/785 |
| 4,799,499 | 1/1989 | Bisping | 128/785 |
| 4,819,662 | 4/1989 | Heil, Jr. et al. | 128/419 P |
| 4,886,065 | 12/1989 | Collins, Jr. | 128/785 |
| 5,002,067 | 3/1991 | Berthelsen et al. | 128/419 P |

Primary Examiner—William E. Kamm
Assistant Examiner—Kennedy J. Schaetzle
Attorney, Agent, or Firm—Peter K. Kontler

[57] ABSTRACT

A cardiac pacemaker lead wherein the helical fixation element and its pointed tip extend beyond the distal end of the insulating sheath for the conductor during implantation into the heart of a patient. In order to prevent damage to tissue during advancement of the fixation element and its tip through blood vessels and into the heart, the tip and preferably a portion of the adjacent convolution of the fixation element are confined in a deformable jacket in the course of the implanting step. The jacket is thereupon extracted by a length of wire or cord, either along the external surface of the sheath or through the axial passageway of the conductor, when the implanting step is completed. The jacket can be made of flexible sheet material or it can consist of closely adjacent convolutions one of which is of one piece with the wire or cord.

34 Claims, 4 Drawing Sheets

CARDIAC PACEMAKER LEAD WITH PROTECTED FIXED TISSUE SECURING MEANS

BACKGROUND OF THE INVENTION

The invention relates to cardiac pacemaker leads, and more particularly to improvements in cardiac pacemaker leads with fixed tissue securing means. Still more particularly, the invention relates to improvements in cardiac pacemaker leads of the type wherein the tissue securing means (such as a fixation helix of platinum alloy or the like) is prevented from damaging the tissue surrounding a body cavity and/or the heart tissue during implantation of the lead.

A cardiac pacemaker lead normally comprises an elongated flexible dielectric sheath with a proximal end at the pacemaker and a distal end at the locus of anchoring in heart tissue, and a flexible conductor which extends through the sheath and has a securing means or terminal projecting beyond the distal end of the sheath and being anchorable in heart tissue. In many instances, the terminal is a so-called fixation helix with a sharp tip which is caused to penetrate into heart tissue in response to rotation of the lead subsequent to completion of the implanting step, e.g., through a blood vessel.

German patent application No. 25 39 553 of Peter Osypka (published Mar. 10, 1977) discloses a cardiac pacemaker lead wherein the terminal of the flexible conductor extends a fixed distance beyond the distal end of the dielectric sheath and constitutes a helix with a sharp tip which is caused to penetrate into heart tissue as soon as the implanting step is completed. The tip of the helix penetrates into the adjacent tissue in response to rotation of the entire lead. Problems can arise during implantation because the sharp tip of the helix is exposed and can cause injury to tissue surrounding the blood vessel or vessels which are selected for implantation of the distal end of the lead into a patient's heart. Furthermore, the tip of the helix can cause injury to a heart valve on its way toward the locus of penetration into heart tissue. The danger of injury is especially pronounced in regions where the distal end of the lead must change the direction of its advancement toward the heart or toward the locus of anchoring in the heart.

Proposals to avoid injury to tissue during implantation of a cardiac pacemaker lead include the provision of a retractable and extendable conductor, i.e., the helix at the distal end of the conductor is retractable into the adjacent end of the insulating sheath and is expelled from the sheath when the implanting step is completed. This normally involves the provision of mating threads in the distal end of the sheath and on the distal end of the conductor, i.e., the conductor can be rotated relative to the sheath in order to retract the tip of its helix during implantation and to expel the tip of the helix when the implanting step is completed and the tip of the helix is ready to penetrate into heart tissue. Reference may be had, for example, to U.S. Pat. No. 4,106,512 granted Aug. 15, 1978 to Hans-Jürgen Bisping and to U.S. Pat. No. 4,217,913 granted Aug. 19, 1980 to Robert G. Dutcher. The patented proposals exhibit the important advantage that the likelihood of injury to tissue during implantation of the cardiac pacemaker lead is reduced or eliminated, even if the helix at the distal end of the conductor is provided with a sharp tip. However, such proposals also exhibit a serious drawback, namely that the pacemaker lead is much more complex because it must be provided with screw threads in the sheath and with complementary screw threads on the conductor. Such treads are needed only and alone during implantation of the lead and subsequent anchoring of the terminal in heart tissue. Since the transverse dimensions of the distal end of the lead are very small, the mating threads must be machined and/or otherwise formed with a high degree of precision which contributes significantly to the cost of the pacemaker lead. Furthermore, the provision of threads at the distal end contributes to the radial dimensions of the lead and hence to the difficulty of implanting such bulky lead in the body of a patient. The bulky distal end of the implanted lead is likely to constitute a cause of irritation of the adjacent wall in a patient's heart which can result in an increase of sensitivity of heart tissue. Still further, the clearances between the mating external and internal threads are likely to establish paths for undesirable escape of blood. In other words, the advantage of avoiding potential injury to tissue during implantation of the cardiac pacemaker lead is achieved by accepting a number of disadvantages including higher cost, more pronounced irritation during implantation due to greater bulk of the distal end of the lead, increased sensitivity of the tissue at the locus of anchoring of the distal end of the electrode, and eventual leakage of body fluid.

European patent application No. A 0 219 608 of (published ) discloses a cardiac pacemaker lead wherein a tubular guide surrounds a flexible conductor and the helix at the distal end of the conductor in the course of the implanting step. The tubular guide has a weakened portion which extends longitudinally of the conductor to the proximal end of the lead and enables the person in charge to separate the guide from the conductor and to extract the separated guide from a patient's body when the implanting step is completed. The thus exposed conductor is then rotated in order to anchor the tip of the helix in the adjacent heart tissue. Such proposal exhibits the advantage that the tubular guide and the conductor need not be provided with mating threads which renders it possible to reduce the radial dimensions of the lead. Moreover, the tubular guide reliably prevents any contact between the tip of the helix at the distal end of the conductor and the adjacent tissue during implantation of the lead, e.g., through selected blood vessels. However, the tubular guide contributes to initial cost of the lead, especially since it must be provided with a weakened portion to permit its separation from the implanted conductor.

European patent application No. 0 337 035 of David W. Mayer et al. (published Oct. 18, 1989) discloses a cardiac pacing electrode wherein the helical fixation element permanently extends beyond the distal end of the dielectric sheath. The exposed fixation element is confined in a spherical bio-compatible covering which is soluble in body fluids. The covering prevents contact between the tip of the fixation element and the tissue during implantation but is supposed to dissolve thereafter and thus permit anchoring of the fixation element in the wall of a patient's heart. Cardiac pacemaker leads which are supplied with such coverings are known as sweat tips and are distributed by Cardiac Pacemakers, Inc. of St. Paul, Minn. A drawback of these pacing electrodes is that the person in charge must permit a certain interval of time to elapse subsequent to completion of the implanting step in order to ensure complete dissolution of the bio-compatible covering prior to rotation of the conductor in order to drive the tip of the fixation element into heart tissue. The exact duration of such interval varies from patient to patient which can create problems, especially when the implanting step involves non-anticipated complications so that the implanting step takes up more time than expected. Thus, the sharp tip of the helical fixation element is likely to injure the tissue during the last stage of implantation.

European patent application No. 0 000 725 of Hans-Jürgen Bisping (published Feb. 21, 1979) discloses a cardiac pacemaker lead wherein the helical terminal at the distal end of the conductor extends beyond the distal end of the tubular sheath in the course of the implanting operation. The tissue surrounding a blood vessel and the heart tissue are protected from injury by a cylindrical body which projects beyond the tip of the helical fixation element during implantation and is thereupon retractable by a cord or wire preparatory to anchoring of the helical terminal in the heart tissue. The cylindrical body has an elastically deformable head to permit extraction from the helical terminal or is provided with external threads meshing with the terminal in the course of the implanting step. In either event, the sharp tip of the helical terminal is not concealed and the likelihood of damage to tissue by the exposed tip depends upon the accuracy of finish of the cylindrical body.

British patent application No. 2 067 411 of Carl Dorning (published Jul. 30, 1981) discloses an electrode lead wherein the distal end of the conductor is dull and the conductor is surrounded by an insulating sheath having a distal end provided with tines which are to anchor the conductor in proper position. A drawback of such proposal is that the distal end of the conductor is not reliably (positively) anchored in the tissue, e.g., in the wall of a patient's heart.

OBJECTS OF THE INVENTION

An object of the invention is to provide a simple and inexpensive cardiac pacemaker lead which need not be provided with a retractable conductor but is still capable of preventing injury to tissue during implantation into the heart of a patient.

Another object of the invention is to provide a cardiac pacemaker lead which exhibits the advantages but does not share the drawbacks of heretofore known cardiac pacemaker leads.

A further object of the invention is to provide a lead wherein the tip of the conductor is ready to be anchored in heart tissue as soon as the implanting step is completed.

An additional object of the invention is to provide a cardiac pacemaker lead which need not employ a biocompatible covering that is soluble in body fluids.

Still another object of the invention is to provide the above outlined cardiac pacemaker lead with novel and improved means for preventing the sharp tip of a helical fixation element from injuring the tissue in a blood vessel and/or in the heart during implantation of the lead.

A further object of the invention is to provide a cardiac pacemaker lead which can be produced at a fraction of the cost of heretofore known leads.

Another object of the invention is to provide a novel and improved method of temporarily confining the tip of a helical fixation element at the distal end of a conductor forming part of a cardiac pacemaker lead.

An additional object of the invention is to provide the cardiac pacemaker lead with novel and improved means for exposing the tip of a helical fixation element upon completion of the implanting step.

Still another object of the invention is to provide a novel and improved method of confining a supply of medication at the distal end of a cardiac pacemaker lead.

Another object of the invention is to provide a cardiac pacemaker lead which can be installed in a simple and time saving manner without risking injury to surrounding tissue in the course of the implanting step.

A further object of the invention is to provide a simple, compact and inexpensive cardiac pacemaker lead wherein the dimensions of the distal end need not be increased for the purpose of avoiding injury to human tissue in the course of the implanting step.

SUMMARY OF THE INVENTION

The invention is embodied in an implantable cardiac pacemaker lead which has a proximal end connectable to a pacemaker and a distal end and comprises an elongated flexible dielectric sheath extending between the proximal and distal ends of the lead and having a distal end at the distal end of the lead, an elongated flexible conductor including a major portion in the sheath and a terminal which is anchorable in the heart tissue of a patient and extends beyond the distal end of the sheath, a jacket which surrounds at least the terminal of the conductor to protect the tissue from injury during implantation of the distal end of the lead into the heart of a patient, and means for separating the jacket from the terminal and for extracting the jacket from the body of a patient upon completion of implantation and preparatory to anchoring of the terminal in heart tissue.

The terminal can include a helix with a pointed tip which is disposed at a fixed distance from the distal end of the sheath. The internal and/or external surface of the properly applied jacket can at least substantially conform to the outline of the terminal of the conductor at the distal end of the lead.

The separating and extracting means can include an elongated flexible element (particularly a length of wire or cord) which extends from the distal end to the proximal end of the lead.

The jacket can include a cap having neighboring convolutions which surround at least the tip of the helix. The radius of curvature of the helix can equal or approximate the radius of curvature of such jacket.

The elongated flexible element of the separating and extracting means can be outwardly adjacent the sheath and extends between the distal and proximal ends of the lead during introduction of the distal end of the lead into the heart of a patient. Alternatively, the conductor can define an elongated passageway which extends from the terminal to the proximal end of the lead, and the flexible element can extend through the passageway. A first end of such flexible element is connected to the jacket, and the other end of the flexible element is accessible at the proximal end of the lead.

The aforementioned helix of the terminal of the conductor can have one or more convolutions and the jacket can include a tube having a closed end which receives the tip of the helix. The tube preferably further includes a section which is adjacent the closed end of the jacket and surrounds at least a portion of the convolution nearest to the pointed tip of the terminal. For example, the section of the tube can surround 25, 33 or 75 percent of the nearest convolution or the entire nearest convolution. The flexible element of the separating and extracting means can be connected to the closed end of the tube which forms part of or constitutes the jacket.

If the jacket includes convolutions, such convolutions preferably surround at least the pointed tip of the helix which forms part of the terminal. Such convolutions can be closely (e.g., immediately) adjacent each other and can be made of any one of a variety of materials, e.g., a filamentary plastic material or metallic wire.

The pointed tip of the helix which forms part of or constitutes the terminal of the conductor can taper in a direction away from the adjacent convolution of the helix. A portion of the jacket can be designed to surround the conical tip and preferably tapers in the same direction as the tip. Such jacket can further comprise a portion which extends beyond the tip and has a diameter which is smaller than or at most equals the diameter of the wire which is used to make the convolution or convolutions of the helix. The diameter of the wire can be larger than the inner or the outer diameter of the aforementioned portion of the jacket.

The elongated flexible element of the separating and extracting means can be of one piece with the jacket. As mentioned above, the flexible element can be connected to that end of the jacket which is located at the tip of the helix forming part of the terminal of the conductor. Alternatively, the flexible element can be connected to the other end of the jacket, e.g., in close or immediate proximity to the distal end of the sheath.

The jacket can extend beyond the tip of the helix and toward the distal end of the sheath.

The improved cardiac pacemaker lead can further comprise at least one transverse wall at the distal end of the sheath, and such wall can be provided with a preferably centrally located opening for the flexible element of the separating and extracting means. The aforementioned passageway of the conductor then extends all the way to such opening and receives the major part of the flexible element, i.e., the flexible element can extend from the jacket, through the opening of the at least one wall, through the passageway and on to the proximal end of the lead. Such lead can further comprise a second transverse wall which is provided in the distal end of the sheath between the at least one transverse wall and the proximal end. The second transverse wall has a preferably centrally located second opening through which the flexible element of the separating and extracting means extends on its way from the opening of the at least one transverse wall toward the proximal end of the lead. The conductor preferably defines a chamber which is disposed between the two transverse walls, and such chamber can be used to store a supply of a medicament. The opening of the at least one transverse wall then constitutes an outlet for gradual dispensing of medicament from the chamber into the heart tissue. At least one of the two transverse walls is preferably elastic, at least in the region around the respective opening.

The novel features which are considered as characteristic of the invention are set forth in particular in the appended claims. The improved cardiac pacemaker lead itself, however, both as to its construction and the mode of implanting the same, together with additional features and advantages thereof, will be best understood upon perusal of the following detailed description of certain presently preferred specific embodiments with reference to the accompanying drawing.

DESCRIPTION OF PREFERRED EMBODIMENTS

Figure 1:
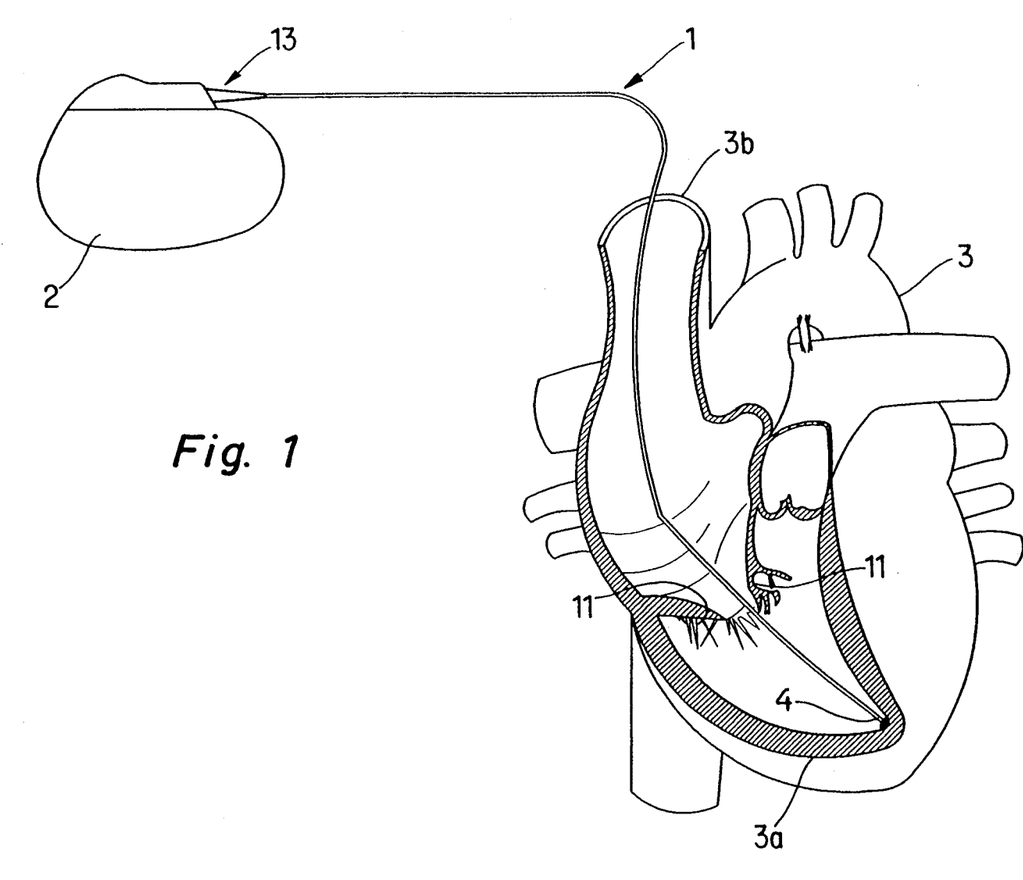
FIG. 1 is a schematic elevational view of a cardiac pacemaker, a schematic partly sectional view of a human heart, and a schematic elevational view of a cardiac pacemaker lead which embodies one form of the invention, the proximal end of which is connected to the pacemaker and the distal end of which is implanted in the heart.

FIG. 1 shows an elongated flexible cardiac pacemaker lead 1 having a proximal end 13 connected to a cardiac pacemaker 2 and a distal end 4 implanted in a human heart 3, namely anchored in the tissue of a wall 3a after having passed through a heart valve 11. The major portion of the lead 1 extends through a series of blood vessels including a vessel 3b.

Figure 2:
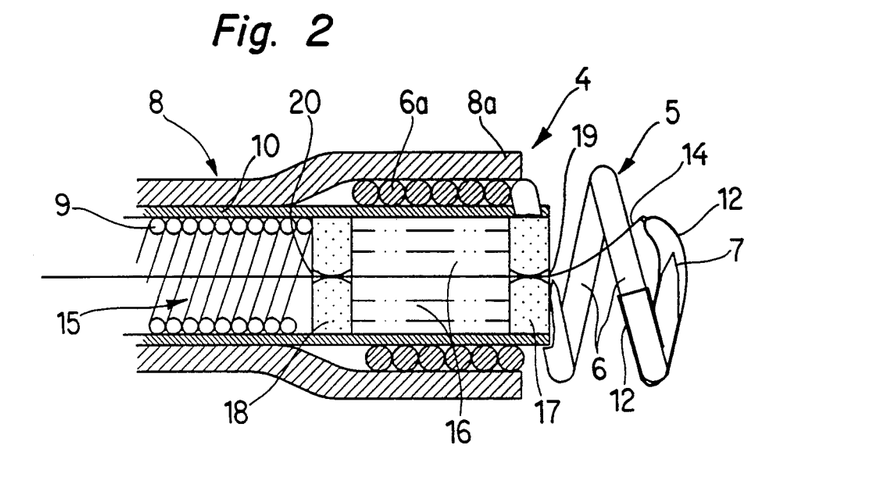
FIG. 2 is a greatly enlarged partly elevational and partly central sectional view of the distal end of the cardiac pacemaker lead of FIG. 1, a tubular hose-like jacket being applied over the pointed conical tip and over the adjacent portion of a helix forming part of the terminal of the elongated flexible conductor of the lead and the elongated flexible element of the separating and extracting means being connected to a portion of the jacket which extends beyond the tip of the helix and toward the distal end of the tubular dielectric sheath of the lead, the flexible element extending through two transverse walls and through an elongated passageway of the conductor toward the proximal end of the lead.

The construction of the parts at the distal end 4 of the cardiac pacemaker lead 1 of FIG. 1 is shown in FIG. 2. The lead 1 comprises a flexible tubular sheath 8 of suitable dielectric material. This sheath extends all the way between the proximal and distal ends 13, 4 of the lead 1, and the latter further comprises an elongated flexible conductor 5 having a major or main portion which is confined in the sheath 8 as well as a terminal or electrode including a helix 6 extending beyond the distal end 8a of the sheath and having an elongated pointed conical tip 7. The major or main portion of the conductor 5 includes a set of helically wound convolutions 9 which extend all the way to the proximal end 13 of the lead 1, a conductive sleeve 10 which surrounds and is electrically connected to the convolutions 9 at the distal end 4, and additional convolutions 6a which surround and are electrically connected to the sleeve 10 within the distal end 8a of the sheath 8. The foremost or rightmost convolution 6a of the major portion of the conductor 5 is integral with the adjacent rearmost or left-hand convolution of the helix 6.

The terminal including the helix 6 and the pointed tip 7 is anchored in the tissue of the wall 3a after the implanting step is completed, i.e., after the distal end 4 has been caused to pass through a series of blood vessels (including the vessel 3b), through the valve 11 and to the position which is shown in FIG. 1. Actual anchoring is effected by rotating the sheath 8 about its longitudinal axis in a counterclockwise direction, as viewed in FIG. 2.

The tip 7 is located at a fixed distance from and forwardly of the distal end 8a of the sheath 8, i.e., the distance of the tip 7 from the sheath does not change during implantation of the distal end 4 of the lead 1 as well as during subsequent anchoring of the helix 6 and its tip 7 in the tissue of the wall 3a. The pitch of the convolution or convolutions of the helix 6 is more pronounced than the pitch of the convolutions 6a which form part of the major portion of the conductor 5; in fact, the convolutions 6a can actually contact each other within the confines of the distal end 8a of the sheath 8. The rather pronounced pitch of the helix 6 is desirable for convenience of anchoring in the wall 3a.

In accordance with a feature of the invention, at least the pointed or sharp tip 7 of the helix 6 of the terminal of the conductor 5 is confined during introduction of the distal end 4 of the cardiac pacemaker lead 1 into the selected portion of the heart 3. The confining means 12 (hereinafter called jacket, tube or cap) which is shown in FIG. 2 surrounds the tip 7 as well as at least a portion of the adjacent foremost convolution of the helix 6, for example, between 25 and 100 percent of the foremost convolution. The arrangement is preferably such that a first or proximal end portion of the jacket 12 (namely the end portion nearest to the distal end 8a of the sheath 8) rather closely hugs the foremost convolution of the helix 6, an intermediate portion of the jacket 12 rather closely hugs the outline of the pointed tip 7, and the closed other end portion of the jacket 12 extends beyond the tip 7 and toward the distal end 8a. It will be seen that the first end portion or section of the jacket 12 (such end portion surrounds the foremost convolution of the helix 6) is a hollow convolution with a radius of curvature matching that of the surrounded portion of the foremost convolution of the helix. This first end portion of the jacket 12 performs the desirable function of ensuring that the position of the jacket does not change at all, or does not change to an appreciable extent, during implantation of the distal end 4 of the lead 1 into the heart of a patient. The median portion of the jacket 12 surrounds the tip 7 and thus prevents the latter from injuring the tissue of a blood vessel and/or the valve 11 and/or any other part of the heart 3 in the course of the implanting step. The material of the jacket 12 which is shown in FIG. 2 is a plastic substance which is sufficiently strong to prevent puncturing by the tip 7 during advancement of the distal end 4 toward the position of FIG. 1. A substantial portion of the helix 6 behind the tip 7 can remain exposed (i.e., it need not be confined in the jacket 12) because such exposed portion merely comprises a portion of a single convolution or more than a full convolution which is not likely to injure the tissue on its way toward and within the heart.

The jacket 12 is not and need not be connected with the dielectric sheath 8. This is desirable and advantageous because, in accordance with a further feature of the invention, the lead 1 comprises means for separating the jacket 12 from the helix 6 and its tip 7 and for extracting the thus separated jacket from the body of the patient. The separating and extracting means comprises an elongated flexible element 14 which can constitute a length of metallic or other wire or an elongated cord of any suitable material. The right-hand end portion of the flexible element 14 is connected with the closed end of the second or distal end portion of the jacket 12 (namely with that end portion which extends beyond the tip 7 and toward the distal end 8a of the sheath 8), and the flexible element 14 thereupon extends through a central opening 19 of a first transverse wall 17 within the confines of the distal end 8a, through a cylindrical chamber 16 between the wall 17 and a second transverse wall 18 between the wall 17 and the proximal end 13 of the lead 1, and thereupon through an elongated axial passageway or channel 15 which is surrounded by the convolutions 9 of the major portion of the conductor 5. The wall 18 has a preferably centrally located opening 20 for the flexible element 14. The left-hand end of the flexible element 14 is accessible at the proximal end 13 of the lead 1 so that the person in charge can exert a pull which suffices to slip the jacket 12 off the helix 6 and its tip 7 and to thereupon extract the thus separated jacket 12 from the body of the patient through the opening 19, chamber 16, opening 20 and passageway 15. The terminal including the helix 6 and its tip 7 can be anchored in the wall 3a as soon as the jacket 12 is retracted into the chamber 16, i.e., as soon as the tip 7 is exposed so that it can penetrate into heart tissue in response to rotation of the sheath 8 and conductor 5. Alternatively, the anchoring step can be carried out upon completion of extraction of the jacket 12 from the passageway 15 in the major portion of the conductor 5. The wall 17 and/or the wall 18 (or at least that portion of the wall 17 and/or 18 which surrounds the respective opening 19 or 20) can be made of an elastomeric material which tends to sealingly engage the flexible element 14 during implantation of the distal end 4 and which tends to seal, or actually completely seals, the respective opening 19 and/or 20 when the extracting step is completed. The chamber 16 can contain a suitable medicament (e.g., a drug which is intended to counter thrombus formation, fibrosis, inflammation or arrythmias or any combination thereof, or to accomplish any other localized purpose). The opening 19 then serves as an outlet for controlled dispensing of the medicament into the tissue of the wall 3a.

An advantage of the feature that the second or distal end portion of the jacket 12 extends beyond the tip 7 of the helix 6 and toward the distal end 8a of the sheath 8 is that such design even further reduces the likelihood of damage to tissue during implantation of the distal end 4 of the lead 1. The closed end of the second end portion of the jacket 12 can be maintained in the position of FIG. 2 by the respective end of the flexible element 14 which is or can be clamped in the opening 19 of the wall 17 and/or in the opening 20 of the wall 18 to thus ensure that it extends beyond the tip 7 and toward the distal end 8a of the sheath 8.

The inner and/or the outer diameter of that end portion of the jacket 12 which extends beyond the tip 7 need not exceed, and can be considerably less than, the diameter of the wire which forms the helix 6.

Figure 3:
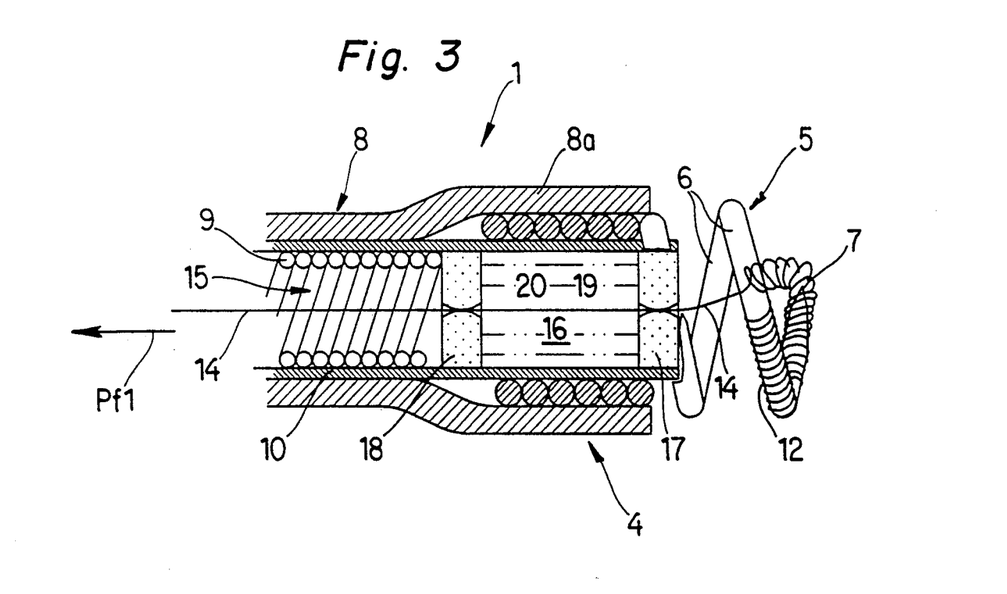
FIG. 3 is a view similar to that of FIG. 2 but showing a modified jacket which consists of closely adjacent convolutions surrounding the pointed tip and the foremost convolution of the helix.

The cardiac pacemaker lead which includes the structure of FIG. 3 is identical with the cardiac pacemaker lead of FIGS. 1-2 except that the jacket 12 of FIG. 3 consists of a set of preferably closely adjacent convolutions of thin wire or filamentary plastic material. Furthermore, the distal end of the elongated flexible element 14 is of one piece with that end portion of the jacket 12 which extends beyond the pointed tip 7 of the helix 6. When the person in charge of extracting the jacket 12 exerts a pull upon the flexible element 14 (in the direction of arrow Pf1), separation of the jacket 12 from the terminal including the helix 6 and the tip 7 actually involves disintegration or transformation of the jacket into a length of wire or cord which is an integral extension of the flexible element 14. The thus converted or transformed jacket 12 can readily pass through the opening 19 of the wall 17, thereupon through the chamber 16 for a supply of medicament, through the opening 20 of the wall 18, and through the passageway 15 on its way toward the proximal end of the lead 1.

The first end portion or section of the jacket 12 which is shown in FIG. 3 can surround at least a certain portion (e.g., 25 percent, one third, 50 percent or 100 percent) of that convolution of the helix 6 which is immediately adjacent and is of one piece with the conical tip 7.

Figure 4:
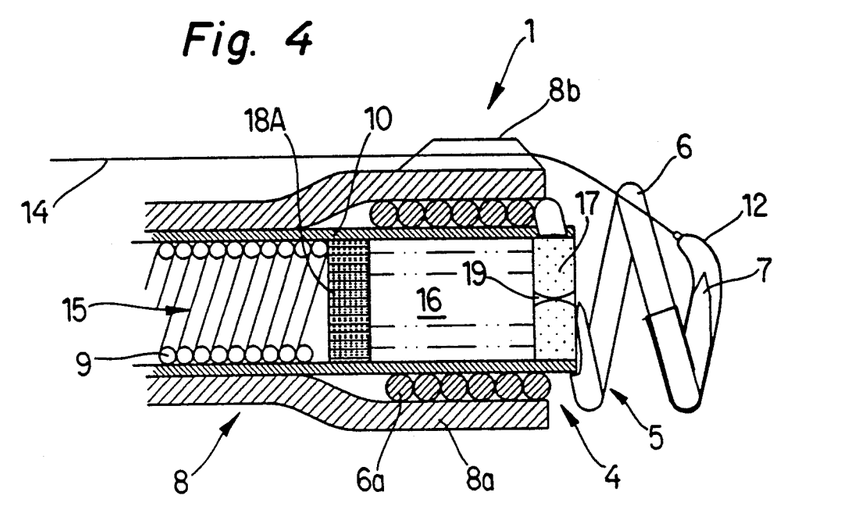
FIG. 4 is a view similar to that of FIG. 2 but showing an elongated flexible element which is outwardly adjacent the dielectric sheath of the lead.

The distal end 4 of the lead 1 which is shown in FIG. 4 is identical with that of FIG. 2 except that the flexible element 14 is outwardly adjacent the sheath 8 and can be guided by one or more external ribs 8b at the distal end 8a of the sheath. The wall 18 of FIG. 2 is replaced by a wall 18A which need not be provided with an opening (corresponding to the opening 20 of the wall 18) because the flexible element 14 does not extend through the opening 19, chamber 16 and passageway 15. The embodiment of FIG. 4 even more reliably prevents penetration of blood into the passageway 15 because the wall 18A does not or need not have an opening.

The wall 18 or 18A is or can be omitted if the distal end 4 of the improved cardiac pacemaker lead 1 need not be provided with a chamber 16 for a medicament. The wall 17 is then replaced by a rigid wall if the flexible element 14 is outwardly adjacent the sheath 8 as shown in FIG. 4. In fact, it is then possible to omit the wall 17 and to provide the distal end 8a of the sheath 8 with an end wall which replaces the wall 17 and through which the wire of the terminal 6, 7 extends between the helix 6 and the nearest convolution 6a. Alternatively, and in order to avoid puncturing of the sheath 8, it is possible to provide the sleeve 10 with a distal end wall which replaces the wall 17 and seals the distal end of the passageway 15 against penetration of body fluids.

Figure 5:
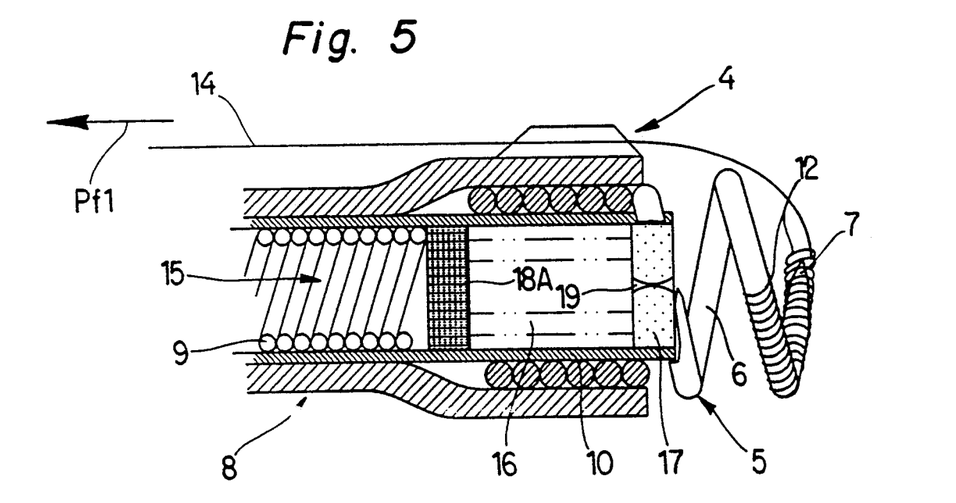
FIG. 5 is a view similar to that of FIG. 3 but showing an enlongated flexible element which is outwardly adjacent the sheath.

The structure which is shown in FIG. 5 is identical with that of FIG. 3 except that the elongated flexible element 14 is outwardly adjacent the sheath 8. Therefore, the apertured wall 18 of FIG. 3 is replaced with a wall 18A which need not have an opening and can be made of a rigid material. The purpose of the wall 18A is to prevent penetration of blood and/or other body fluids into the passageway 15 within the confines of the coiled part 9 of the main or major portion of the conductor 5.

Figure 6:
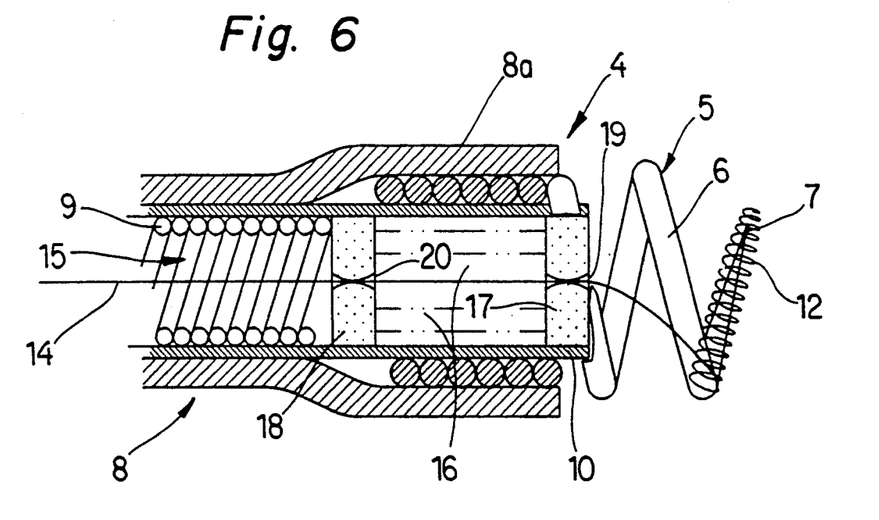
FIG. 6 is a view similar to that of FIG. 5 but showing a flexible element which extends through the conductor and is connected to the proximal end of the jacket.
Figure 7:
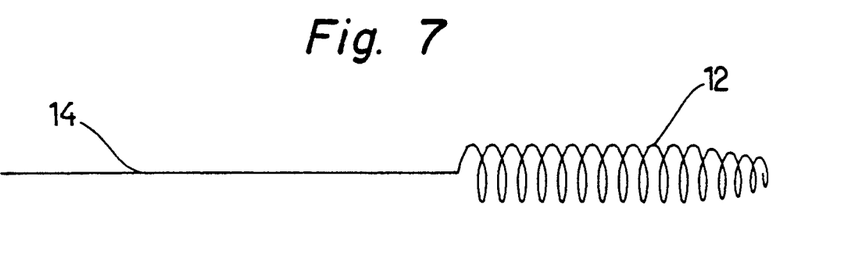
FIG. 7 shows the jacket and the flexible element of FIG. 6 prior to application of the jacket over the tip of the helix.

The difference between the structures of FIGS. 3 and 6 is that the jacket 12 which is shown in FIG. 6 surrounds only the tip 7 of the terminal which includes the helix 6, and that the distal end of the elongated flexible element 14 is of one piece (see also FIG. 7) with that end portion of the jacket 12 (i.e., with the rearmost convolution of the jacket) which is remote from the free end of the tip 7. The distance between the convolutions of the jacket 12 which is shown in FIG. 7 is exaggerated for the sake of clarity; in actual practice, the convolutions are closely or immediately adjacent each other to reduce the likelihood of penetration of the free end of the tip 7 through the jacket and eventual damage to the tissue during implantation of the cardiac pacemaker lead which embodies the structure of FIG. 6. The diameters of convolutions of the jacket 12 of FIGS. 6 and 7 decrease in a direction away from the distal end of the flexible element 14; this ensures that the internal and/or the external surface of the jacket 12 rather closely follows the outline of that part (i.e., at least the tip 7) of the terminal of the conductor 5 which extends beyond the distal end 8a of the dielectric sheath 8. The just described configuration of the jacket 12 reduces the likelihood of slippage of the convolutions of this jacket onto the adjacent convolution of the helix 6 during implantation of the distal end 4 of FIG. 6 into the body of a patient. The same holds true for all other embodiments of the improved lead 1 and its jacket 12, i.e., each and every jacket can be designed in such a way that it is not likely to expose the tip 7 during implantation because the jacket cannot slide along the helix 6 toward the distal end 8a of the respective sheath 8.

An advantage of the jackets 12 which are shown in FIGS. 3, 5, 6 and 7 is that the making of the separating and extracting means (elongated flexible element 14) and of the respective jacket 12 is simplified due to the fact that the distal end of the flexible element 14 is or can be of one piece with the one or the other end portion of the jacket. This eliminates the rather delicate step of reliably affixing the distal end of the flexible element 14 to the selected end portion of the jacket.

The combination of the flexible element 14 and jacket 12 in the embodiment of FIG. 5 exhibits the advantage that the flexible element 14 need not extend through the conductor 5 and that the jacket 12 can be converted into a length of thin wire or cord in a particularly simple and reliable manner by the expedient of exerting upon the flexible element 14 a pull in the direction of arrow Pf1. The jacket 12 of FIGS. 3, 5 and 6 can be formed in advance (see FIG. 7) so that it is merely slipped onto the tip 7 of the terminal including the helix 6 prior to introduction of the distal end 4 of the respective lead 1 into a blood vessel and thence into the heart of a patient. It is even possible to impart of the jacket 12 of FIG. 3, 5 or 6 a helical shape prior to its application over the respective tip 7.

An important advantage of the improved cardiac pacemaker lead is its simplicity. Thus, the terminal 6, 7 of the conductor 5 can be fixedly mounted relative to the distal end 8a of the sheath 8 (i.e., the pointed tip 7 of the helix 6 can permanently extend a fixed distance beyond the distal end 8a) without risking damage to the tissue during implantation of the distal end 4 of the lead. This is accomplished by the simple expedient of employing a jacket 12 which confines the tip 7 (or the tip 7 and the adjacent portion of the terminal of the conductor 5) during implantation of the distal end 4, and by employing means (14) for separating the jacket 12 from and for (simultaneously or thereafter) extracting the jacket out of the body of a patient so that the terminal 6, 7 of the conductor 5 is fully exposed and is ready to be anchored in heart tissue by rotating the sheath 6 and the terminal 6, 7 of the conductor 5 in a clockwise or in a counterclockwise direction. The jacket 12 may but need not surround the entire terminal of the conductor 5; all that counts is to ensure that the terminal cannot cause damage to the tissue of a blood vessel and/or heart during implantation of the distal end 4.

Since the conductor 5 need not be rotatable and axially movable relative to the sheath 8, the improved lead 1 is simpler, less expensive and more compact (particularly at the distal end 4) than a conventional cardiac pacemaker lead wherein the terminal or electrode of the conductor is retractible into the sheath for the purposes of safe implantation.

The improved lead also exhibits important advantages over cardiac pacemaker leads of the type described in the aforediscussed European patent application No. 0 337 035 of Mayer et al. who propose to employ a spherical bio-compatible covering for the helical fixation element of the conductor. Thus, a person in charge of manipulating the flexible element 14 and the jacket 12 of the improved lead 1 can determine the exact timing of anchoring the terminal 6, 7 in heart tissue, whereas a person in charge of anchoring the fixation element of the lead of Mayer et al. must await dissolution of the bio-compatible covering. Moreover, and if the implantation is difficult and time-consuming, the covering is likely to become dissolved prior to completion of the implanting step so that the sharp fixation element is exposed in the course of the implanting step and is likely to damage the tissue of a blood vessel or the heart of the patient.

Another important advantage of the improved lead is that the jacket 12 need not be self-supporting, i.e., the jacket can be made of a readily deformable material (such as relatively thin plastic sheet material or convolutions of thin or extremely thin metallic wire, plastic filament, cord or the like) because the rigid terminal 6, 7 of the conductor 5 ensures that the jacket 12 assumes and retains an optimal shape in the course of the actual implanting step. A relatively thin jacket 12 (which can be collapsed into an extremely small package for extraction in a manner as described in connection with FIGS. 2 and 4 or which can be simply converted into a length of wire or cord in a manner as described with reference to FIGS. 3, 5, 6 and 7) can be extracted from the body of a patient in an extremely simple, time-saving and convenient manner, either along the external surface of the dielectric sheath 8 or through the passageway 15 of the conductor 5.

The dimensions of the jacket 12 can be selected in such a way that it undergoes a certain amount of expansion while it is being slipped over the tip 7 and/or over a portion of or the entire convolution of the helix 6 immediately adjacent the tip 7. This reduces the likelihood of undesirable shifting of the jacket 12 in the course of the actual implanting step without necessitating the exertion of a substantial effort for the purpose of extracting the jacket upon completion of the implanting step. In other words, it is often desirable to mount the jacket 12 on the terminal 6, 7 of the conductor 5 in such a way that the thus established engagement can be termed a form-locking connection involving a desirable frictional engagement between the internal surface of the jacket and the external surface of the terminal. Such engagement ensures that the thus deformed or shaped jacket 12 rather closely follows the outline of the confined part of the terminal 6, 7 and is thus even less likely to permit the tip 7 from damaging the tissue during implantation of the distal end 4 into the heart of a patient. The establishment of a rather pronounced frictional engagement between a portion of or the entire jacket 12 on the one hand, and a portion of or the entire terminal 6, 7 on the other hand, does not unduly affect the ease of separating and extracting the jacket upon completion of the implanting step. A jacket 12 which is made of closely adjacent convolutions (FIGS. 3, 5, 6 and 7) has been found to be particularly suitable to ensure close conformance of its internal and external surfaces to adjacent confined portions of the terminal 6, 7.

The feature that the diameter of that end portion of the jacket 12 which extends beyond the tip 7 of the terminal 6, 7 is less than the diameter of the wire which is used to make the helix 6 is that such jacket is even less likely to permit the tip 7 to damage the tissue during introduction of the distal end 4 into the heart of a patient. Thus, that end portion of the jacket 12 which extends beyond the tip 7 is not likely to be shifted relative to and slipped onto the tip 7 during implantation of the distal end 4 so that the free end of the tip 7 remains confined in the jacket during advancement toward the selected wall 3a of a patient's heart.

It is often preferred to connect the flexible element 14 to (or to make this flexible element of one piece with) that end portion of the jacket 12 which extends beyond the tip 7. This enables the flexible element 14 to maintain the respective end portion of the jacket 12 in an optimum orientation to prevent penetration of the tip 7 through the jacket 12 during advancement of the distal end 4 toward and into the heart 3. Moreover, this simplifies separation and extraction of the jacket 12, especially if the jacket 12 is made of closely adjacent convolutions and/or is to be extracted along the external surface of the sheath 8 (see FIGS. 4 and 5).

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. An implantable cardiac pacemaker lead having a proximal end and a distal end and comprising an elongated flexible dielectric sheath extending between said ends and having a distal end at the distal end of the lead; an elongated flexible conductor including a major portion in said sheath and terminal means for anchoring in the heart tissue of a patient and extending beyond the distal end of said sheath; a jacket surrounding at least the terminal means of said conductor to protect the tissue from injury during implantation of the distal end of the lead, said terminal means including a helix having a pointed tip and said jacket including a cap having neighboring convolutions which surround at least the tip of said helix; and means for separating said jacket from said terminal means and for extracting the jacket from the body of a patient upon completion of implantation and preparatory to anchoring of said terminal means in heart tissue.

2. The lead of claim 1, wherein said separating and extracting means includes an elongated flexible element which extends from the distal end to the proximal end of the lead.

3. The lead of claim 1, wherein said helix has a first radius of curvature and said jacket has a second radius of curvature at least approximating said first radius.

4. The lead of claim 1, wherein said separating and extracting means includes an elongated flexible element which is outwardly adjacent said sheath and extends from said terminal means to said proximal end.

5. The lead of claim 1, wherein said conductor defines a passageway extending from said terminal means to said proximal end and said separating and extracting means includes an elongated flexible element which extends through said passageway, said flexible element having a first end connected to said jacket and a second end accessible at said proximal end.

6. The lead of claim 1, wherein said separating and extracting means comprises an elongated flexible cord.

7. The lead of claim 1, wherein said separating and extracting means comprises an elongated flexible wire.

8. The lead of claim 1, wherein said separating and extracting means comprises an elongated flexible element which is of one piece with said jacket.

9. The lead of claim 1, wherein said jacket has an end portion at said tip, said separating and extracting means comprising an elongated flexible element which is connected with the end portion of said jacket.

10. The lead of claim 1, wherein said jacket includes a first end portion at said tip and a second end portion spaced apart from said first end portion, said separating and extracting means comprising an elongated flexible element connected with the second end portion of said jacket.

11. The lead of claim 10, wherein said flexible element is of one piece with said jacket.

12. The lead of claim 1, wherein said jacket includes an end portion extending beyond said tip and toward the distal end of said sheath.

13. The lead of claim 1, further comprising at least one transverse wall at the distal end of said sheath, said at least one wall having an opening and said conductor defining an elongated passage between said proximal end and said opening, said separating and extracting means comprising an elongated flexible element extending from said jacket to said proximal end through said opening and said passageway.

14. An implantable cardiac pacemaker lead having a proximal end and a distal end and comprising an elongated flexible dielectric sheath extending between said ends and having a distal end at the distal end of the lead; an elongated flexible conductor including a major portion in said sheath and terminal means for anchoring in the heart tissue of a patient and extending beyond the distal end of said sheath, said conductor defining a passageway estending from said terminal means to said proximal end; a jacket surrounding at least the terminal means of said conductor to protect the tissue from injury during implantation of the distal end of the lead; and means for separating said jacket from said terminal means and for extracting the jacket from the body of a patient upon completion the implantation and preparatory to anchoring of said terminal means in heart tissue, said separating and extracting means including an elongated flexible element which extends through said passageway, said flexible element having a first end connected to said jacket and a second end accessible at said proximal end.

15. The lead of claim 14, wherein said terminal means includes a helix having a pointed tip disposed at a fixed distance from the distal end of said sheath.

16. The lead of claim 14, wherein said terminal means has a predetermined outline and said jacket has internal and external surfaces at least one of which at least substantially conforms to the outline of said terminal means.

17. The lead of claim 14, wherein said terminal means includes a helix having a pointed tip and said jacket includes a cap having neighboring convolutions which surround at least the tip of said helix.

18. The lead of claim 14, wherein said terminal means includes a helix having a pointed tip and said jacket includes convolutions which surround at least the tip of said helix.

19. The lead of claim 14, wherein said terminal means includes a helix having at least one convolution and a substantially conical tip which is integral with and tapers in a direction away from said at least one convolution, said jacket having a portion which surrounds said tip and tapers in said direction.

20. An implantable cardiac pacemaker lead having a proximal end and a distal end and comprising an elongated flexible dielectric sheath extending between said ends and having a distal end at the distal end of the lead; an elongated flexible conductor including a major portion in said sheath and terminal means for anchoring in the heart tissue of a patient and extending beyond the distal end of said sheath, said terminal means including a helix having at least one convolution and a pointed tip at a fixed distance from the distal end of said sheath; a jacket surrounding at least the terminal means of said conductor to protect the tissue from injury during implantation of the distal end of the lead, said jacket including a tube having a closed end receiving said tip and a section adjacent said closed end and surrounding at least a portion of said at least one convolution; and means for separating said jacket from said terminal means and for extracting the jacket from the body of a patient upon completion of implantation and preparatory to anchoring of said terminal means in heart tissue.

21. The lead of claim 20, wherein said section of said tube surrounds at least 25 percent of said at least one convolution.

22. The lead of claim 20, wherein said separating and extracting means comprises an elongated flexible element connected to the closed end of said tube and extending to said proximal end.

23. An implantable cardiac pacemaker lead having a proximal end and a distal end and comprising an elongated flexible dielectric sheath extending between said ends and having a distal end at the distal end of the lead; an elongated flexible conductor including a major portion in said sheath and terminal means for anchoring in the heart tissue of a patient and extending beyond the distal end of said sheath, said terminal means including a helix having a pointed tip; a jacket surrounding at least the terminal means of said conductor to protect the tissue from injury during implantation of the distal end of the lead, said jacket including convolutions which surround at least the tip of said helix; and means for separating said jacket from said terminal means and for extracting the jacket from the body of a patient upon completion of implantation and preparatory to anchoring of said terminal means in heart tissue.

24. The lead of claim 23, wherein said convolutions are closely adjacent each other.

25. The lead of claim 23, wherein said convolutions consist of filamentary plastic material.

26. The lead of claim 23, wherein said convolutions consist of metallic wire.

27. An implantable cardiac pacemaker lead having a proximal end and a distal end and comprising an elongated flexible dielectric sheath extending between said ends and having a distal end at the distal end of the lead; an elongated flexible conductor including a major portion in said sheath and terminal means for anchoring in the heart tissue of a patient and extending beyond the distal end of said sheath, said terminal means including a helix having at least one convolution and a substantially conical tip which is integral with and tapers in a direction away from said at least one convolution; a jacket surrounding at least the terminal means of said conductor to protect the tissue from injury during implantation of the distal end of the lead, said jacket having a portion which surrounds said tip and tapers in said direction; and means for separating said jacket from said terminal means and for extracting the jacket from the body of a patient upon completion of implantation and preparatory to anchoring of said terminal means in heart tissue.

28. The lead of claim 27, wherein said jacket further includes a portion which extends beyond said tip and has a first diameter, said at least one convolution consisting of wire having a second diameter at least matching said first diameter.

29. The lead of claim 27, wherein said jacket further includes a portion which extends beyond said tip and has a predetermined inner diameter, said at least one convolution consisting of wire having a second diameter at least matching said inner diameter.

30. An implantable cardiac pacemaker lead having a proximal end and a distal end and comprising an elongated flexible dielectric sheath extending between said ends and having a distal end at the distal end of the lead; an elongated flexible conductor including a major portion in said sheath and terminal means for anchoring in the heart tissue of a patient and extending beyond the distal end of said sheath, a jacket surrounding at least the terminal means of said conductor to protect the tissue from injury during implantation of the distal end of the lead; means for separating said jacket from said terminal means and for extracting the jacket from the body of a patient upon completion of implantation and preparatory to anchoring of said terminal means in heart tissue; and at least one transverse wall at the distal end of said sheath, said at least one wall having an opening and said conductor defining an elongated passage between said proximal end and said opening, said separating and extracting means comprising an elongated flexible element extending from said jacket to said proximal end through said opening and said passageway.

31. The lead of claim 30, further comprising a second transverse wall provided in said distal end of said sheath between said at least one wall and said proximal end, said second wall having a second opening and said flexible element extending through said second opening.

32. The lead of claim 31, wherein said conductor defines a chamber between said walls.

33. The lead of claim 32, wherein said chamber is arranged to store a supply of medicament and said opening of said at least one wall constitutes an outlet for gradual dispensing of a medicament from said chamber.

34. The lead of claim 31, wherein at least one of said walls is elastic, at least in the region around the respective opening.

* * * * *